United States Patent [19]

Alphonse

[11] 4,096,756
[45] Jun. 27, 1978

[54] VARIABLE ACOUSTIC WAVE ENERGY TRANSFER-CHARACTERISTIC CONTROL DEVICE

[75] Inventor: Gerard Argant Alphonse, Princeton, N.J.

[73] Assignee: RCA Corporation, New York, N.Y.

[21] Appl. No.: 812,706

[22] Filed: Jul. 5, 1977

[51] Int. Cl.² .................... G01N 29/00; H03H 9/26; H01L 41/10
[52] U.S. Cl. ........................................ 73/609; 73/632; 310/317; 310/334; 333/72
[58] Field of Search ................ 73/632, 628, 641, 609; 310/317, 334; 333/72

[56] References Cited
U.S. PATENT DOCUMENTS

3,233,466   2/1966   Shaw, Jr. ..................... 310/317 X
3,285,074   11/1966  Elazar ............................ 73/517 R Primary Examiner—James J. Gill
Attorney, Agent, or Firm—H. Christoffersen; Samuel Cohen; George J. Seligsohn

[57] ABSTRACT

The effective thickness of a piezoelectric unit comprising a plurality of contiguous layers is varied by selectively short circuiting one or more layers with switch means. This varies the electro-acoustic properties at an operating frequency that is exhibited between the respective acoustic ports of the unit and an electrical circuit coupled across the electric port of the unit. Specific embodiments of such a unit, switch means and electrical circuit are useful in a control device for acoustic-wave propagating systems.

12 Claims, 9 Drawing Figures

VARIABLE ACOUSTIC WAVE ENERGY TRANSFER-CHARACTERISTIC CONTROL DEVICE

This invention relates to variable acoustic wave energy transfer-characteristic control devices and, more particularly, to such devices using multiple piezoelectric layers.

It is known that a single-layered piezoelectric plate with its opposite faces metallized forms a three-port device. The three ports comprise one electrical port between the respective electrodes formed by the two metallized surfaces, across which a voltage can exist, the two mechanical ports consisting of each of the respective faces of the plate, over which a force can exist. The impedance of the electrical port depends upon the boundary conditions at the two electrodes. By closing and opening a switch connected across the electrodes, the electrical port can be shorted or opened. Either of the two mechanical ports is in the open-circuit condition when the corresponding piezoelectric plate face is placed against a "rigid" wall (i.e. a wall having a very high acoustic impedance) and is in the short-circuit condition when it is in a vacuum or when it is in contact with a very low acoustic impedance, such as air.

In the past, such single-layered piezoelectric plates, with respective electrodes on each of its opposite faces, have been used acoustically mainly as electro-acoustic transducers for transmitting and/or receiving sonic or ultrasonic wave energy. More recently, it has been proposed that one or more of such single-layered piezoelectric plates, along with appropriate electrical control circuitry, be placed in the path of a propagating acoustic wave and be used as a variable acoustic wave energy transfer-characteristic control device exhibiting variable acoustic reflection and transmission coefficients. Such variable acoustic wave energy transfer-characteristic control devices are described in the following articles:

(1) E. K. Grishchenko and L. I. Kholod, "Acoustic Impedance and Transmissivity of and Electrically Loaded Piezoelectric Element," Sov. Phys. Acoust. 21, p. 252, 1975.
(2) E. K. Grishchenko, "Acoustic Analog of the Electro-Optic Shutter," Sov. Phys. Acoust. 21, p. 511, 1975.
(3) E. B. Krivin, "Reflection of a Plane Sound Wave from an Electrically Loaded Piezoelectric Layer," Sov. Phys. Acoust. 21, p. 144, 1975.

Article (1) discusses a device with a series of two contiguous piezoelectric plates, each plate having an acoustic thickness equal to one-half of a given acoustic wavelength. The first plate acts as a conventional transducer for generating or receiving acoustic wave energy. The second plate, which has a variable Q circuit electrically connected across the electrodes thereof, is situated between the first plate and an acoustic propagating medium and operates as a control element for controlling the acoustic transmission of the wave energy to or from the propagating medium as a function of the Q of the variable Q circuit. Specifically, the transmission approaches unity as the Q approaches zero and the transmission approaches zero as the Q approaches infinity. However, in practice, the range between the maximum and minimum Q (and, hence, the range between the maximum and minimum acoustic transmissivity) is limited.

Article (2) suggests the use of a control device, of the type described in Article (1), as an acoustic shutter for selectively transmitting or reflecting incident acoustic wave energy. Article (3) analyzes more complex electrically-controlled acoustic networks which may be composed of a plurality of half-wave piezoelectric plates. Each individual one of the piezoelectric plates in Article (3) has associated therewith its own variable electrical load connected across the electrodes thereof, so that each piezoelectric plate together with its associated electrical load operates as a separate variable acoustic impedance of the overall acoustic network. Article (3) suggests that such a controllable acoustic network may be employed as an acoustic gate by appropriately switching the state of the respective electrical load of each individual piezoelectric plate of the acoustic network. Thus, in article (3), the acoustic network is comprised of a plurality of interconnected substantially independent single-layered piezoelectric plates, each exhibiting an effective impedance determined by its own electrical load.

The present invention makes use of a variable acoustic wave energy transfer characteristic control device including a piezoelectric unit which comprises a plurality of contiguous layers of piezoelectric material which defines two outer faces and define an interface between each pair of adjacent ones of the contiguous layers. Each of the layers has a respective specified thickness. The piezoelectric unit also comprises first and second electrodes respectively at the outer faces and at least one additional electrode at each interface. The variable acoustic wave energy transfercharacteristic control device also includes an electrical circuit connected across the first and second electrodes and switch means for selectively connecting at least one additional electrode to another electrode which selectively short circuits at least a portion of at least one of the layers of the piezoelectric unit. Thus, the multi-layered piezoelectric unit together with the given electrical circuit and the switch means operate as a unitary acoustic wave energy control device having at least two states. Also disclosed herein are various acoustic wave propagating systems incorporating such a unitary acoustic wave energy control device.

Figure 1:
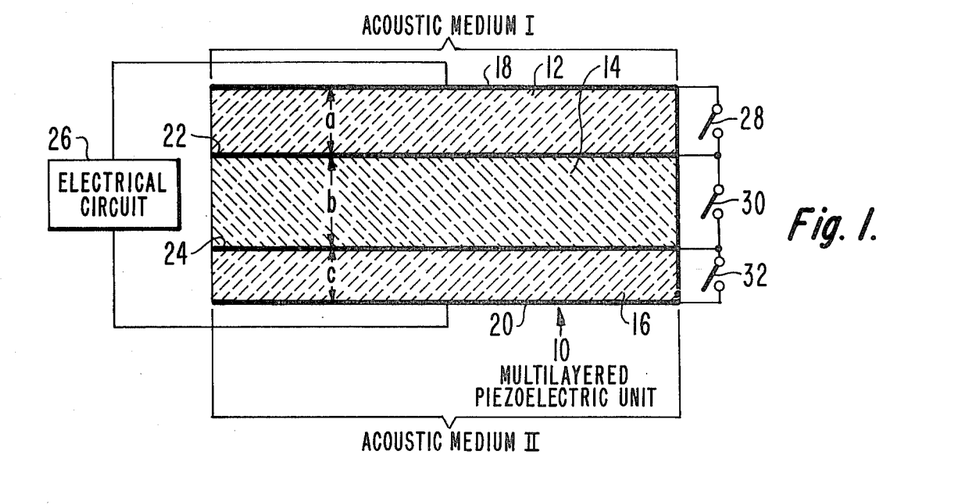
FIG. 1 is a schematic diagram of a generalized embodiment of a variable acoustic wave energy transfer-characteristic control device incorporating the principles of the present invention.

Referring now to FIG. 1, multi-layered piezoelectric unit 10 may comprise two or more contiguous layers of piezoelectric material (such as the three layers, 12, 14 and 16 shown in FIG. 1). Layer 12 has a first specified thickness $a$; layer 14 has a second specified thickness $b$, and layer 16 has a third specified thickness $c$.

Unit 10 further includes first electrode 18 at the upper outer face thereof, second electrode 20 at the lower outer face thereof, additional electrode 22 at the interface between layers 12 and 14, and additional electrode 24 at the interface between layers 14 and 16. Electrical circuit 26 is connected across first and second electrodes 18 and 20. Electrical circuit 26 may include one or more reactive and/or resistive impedance elements and, in any given case, may or may not include a voltage source and/or a detector. Switch means comprising first switch 28, second switch 30 and third switch 32 connected to electrodes 18, 20, 22 and 24, may be utilized to selectively short circuit one or more of piezoelectric layers 12, 14 and 16. In practice, switches 28, 30 and 32 may comprise electronic gates. The upper outer face of control device 10 is in effective contact with acoustic propagating medium I and the lower outer face of unit 10 is in effective contact with acoustic propagating medium II. In any given case, mediums I and II may be the same or may be different from each other.

The operation of the generalized embodiment of the present invention shown in FIG. 1 makes use of one or more of the following electro-acoustic principles known in the art: An electro-acoustic transducer transforms electrical parameters into mechanical parameters and mechanical parameters into electrical parameters. In this transformation the electrical parameters of voltage, current, inductance, capacitance and electrical resistance correspond respectively with the mechanical parameters of force, velocity, mass, compliance and mechanical resistance. The piezoelectric plate, per se, comprises a mechanical resonant cavity having a resonant frequency determined by the effective thickness of the piezoelectric plate. Therefore, the piezoelectric plate may operate as a mechanical band-pass filter over a frequency band centered at an acoustic frequency determined by the thickness of the piezoelectric plate. The band-pass characteristics of such a filter depend both on the mechanical characteristics of the piezoelectric material itself and also on the mechanical transformation of any electrical generating and/or load circuit connected across the piezoelectric plate, due to the piezoelectric properties thereof.

By electrically short circuiting the opposite surfaces of a piezoelectric plate of given thickness, the piezoelectric properties thereof can be inhibited. This is true because, in accordance with Gauss' law, no net electric field can exist within a volume defined by two spaced equipotential surfaces. Thus, a plate of otherwise piezoelectric material operates as purely acoustic transmission medium when its opposite surfaces are electrically short circuited.

Figures 2, 3:
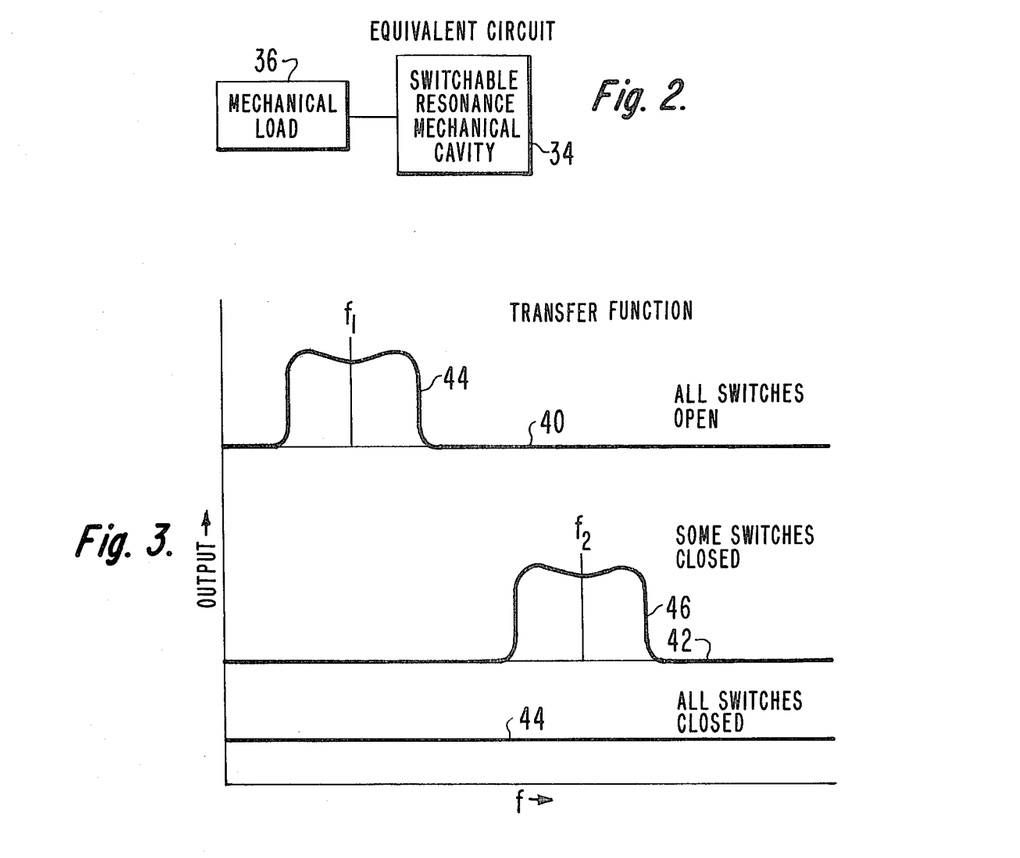
FIG. 2 is a block diagram of the equivalent mechanical circuit of the control device of FIG. 1.
FIG. 3 illustrates the change in the transferfunction characteristic of the control device of FIG. 1 in accordance with the switch condition of the switches thereof.

FIG. 2 shows the mechanical equivalent circuit of the arrangement shown in FIG. 1. The mechanical equivalent circuit of multi-layered piezoelectric unit 10 together with switches 28, 30 and 32 comprises switchable resonant mechanical cavity 34, while mechanical load 36 coupled thereto comprises the resultant mechanical equivalent of both the transferred load impedance of electrical circuit 26 connected across the electrical port of device 10 and the direct mechanical load impedance of acoustic medium I and II connected respectively to the two mechanical ports of unit 10. When all of switches 28, 30 and 32 are open, the effective depth of resonant mechanical cavity 34 is at its maximum, $a + b + c$. In this case, resonant frequency $f_1$, shown in graph 40 of FIG. 3, of cavity 34 is relatively at its lowest. When some, but not all, of the switches 28, 30 and 32 are closed, the effective depth of cavity 34 is reduced being determined in accordance with the sum of the thicknesses of only those layers of unit 10 which are not short circuited. Thus, for example, with only switch 28 open, the effective depth of cavity 34 is determined solely by the thickness $a$ of layer 12. In a similar manner by closing other arrangements of some, but not all of switches 28, 30 and 32, the effective cavity depths 34 can be simulated. As there are three layers, the switches can assume $2^3$ or 8 combinations of positions corresponding to eight cavity depths determined by the respective thicknesses $a$, $b$, $c$, $a + b$, $a + c$, $b + c$, $a + b + c$ and zero. The resonant frequency of cavity 34 at any particular time is equal to some value $f_j$ which is determined by the reduced effective thickness of cavity 34 at that time. This value $f_j$ is always higher than frequency $f_1$, obtained when all switches are open. Graph 46 of FIG. 3 illustrates the resonant frequency $f_2$ (that is, $j=2$) for one particular thickness less than $a + b + c$. Graph 44 of FIG. 3 shows that when all of switches 28, 30 and 32 are closed, the effective thickness of unit 10 is zero. In this last case, unit 10 no longer operates at a resonant cavity. Instead, with all switches closed, unit 10 operates only as a length of acoustic transmission medium.

The pass-band characteristics 44 of graph 40 and pass band characteristics 46 of graph 42 of FIG. 3 between its acoustic and electric ports are determined both by the impedance characteristics of the piezoelectric material making up the effective cavity portions of unit 10 and the impedance characteristics of electrical circuit 26 connected across the electric port thereof as shown in FIG. 1. Thus, unit 10 may be utilized as a switchably-turnable acoustic filter for selecting any one of a plurality of frequency sub-bands as an output from unit 10, from incident broad-band acoustic wave energy applied as an input thereto. Alternatively, where the incident acoustic wave energy input is within at least a certain one of the switchable pass-bands, and is absent from another one of the switchable pass-bands, unit 10 may be employed as a gate which is open when the switch means thereof are set to provide the certain pass-band and is closed when the switch means thereof are set to provide the other pass-band.

In addition to the frequency selective and/or gating functions of unit 10, the amount of incident acoustic wave energy input within the pass-band which would normally be transmitted, but instead is actually reflected and/or absorbed, can also be controlled. More specifically, the effective relative impedance of unit 10 with respect to the impedance of acoustic medium I may be adjusted by means of electrical circuit 26 to control the fraction of input wave energy which is reflected from the upper face of unit 10. Further, the resistive component of the impedance of electrical circuit 26 may be adjusted to absorb more or less of the incident acoustic wave energy input that was not reflected, but entered unit 10. In this manner, the effective attenuation provided by unit 10 can be controlled.

Although, as is discussed above, the piezoelectric characteristics of short circuited layers of control device 10 are inhibited, the short circuited layers may still play a significant role in determining the time delay characteristics of control device 10 as a transmission medium and, even more important, the short circuited layers may operate as impedance transformers inserted between the resonant cavity formed by one or more unshorted layers and either a respective one of the acoustic mediums effectively contacting the outer layers of unit 10 or, alternatively, another resonant cavity formed by one or more other unshorted layers. In more quantitative terms, $$Z = Z_0 \frac{1 + j Z_R \tan \beta T}{Z_R + j \tan \beta T} \quad (1)$$

where, $Z$ is the impedance presented at one face of a short-circuited layer;

$Z_O$ is the impedance of the layer material itself $$Z_R = Z_O/Z_L$$

$Z_L$ is the impedance of the medium in contact with the other face of the short-circuited layer.

$\beta = 2\pi/\lambda$ $\lambda$ is the wavelength of the acoustic energy within the layer $T$ is the thickness of a short circuited layer or layers One important case is where the thickness T is an odd quarter-wavelength at the frequency of the acoustic wave energy. In this case equation (1) reduces to:

$$Z = Z_0^2/Z_L \quad (2)$$

The value of impedance Z in this case can be extremely large. For instance, in the practical case where the propagating medium is water and the layer material is PZT-4, the relatively low acoustic impedance $Z_L$ of water ($1.5 \times 10^6$ kg/m sec) is transformed to an extremely high value of acoustic impedance Z ($771 \times 10^6$ kg/m² sec) by the intermediate acoustic impedance $Z_O$ of PZT — 4 ($34 \times 10^6$ kg/m²sec). Thus, an odd quarter-wave thick layer of sufficiently high intrinsic impedance may be utilized to transform a soft wall into a rigid wall (or vice versa). Alternatively, such an odd quarter-wave thick layer may be used to match any impedance Z to a different load impedance $Z_L$, when $Z_O$ is chosen to be equal to the geometric means between Z and $Z_L$.

A second important case is where the thickness T of the short circuited layer is an odd number of half-wavelengths. In this second case, equation (1) reduces to:

$$Z = Z_L \quad (3)$$

In this latter case, the short circuited layer has absolutely no effect. It behaves on impedance as if it has zero thickness (except for a 180° phase shift and inherent time delay not evident from equation 3), regardless of the value of $Z_O$.

Multi-layered piezoelectric unit 10 may also be employed as a transducer (i.e. to generate an acoustic wave in response to an applied electrical signal and/or to detect an electric signal in response to an applied acoustic wave). Efficient electro-acoustic conversion may be accomplished when the effective thickness of the non-short-circuited layers of unit 10 is an odd number of quarter-wavelengths at an operating frequency equal to the resonant cavity frequency, if (and only if) one face of the cavity is rigid and acts substantially as a perfect acoustic mirror. In this case, acoustic energy can flow easily from the acoustic port defined by the other face to the electrical port, and vice versa. Furthermore, maximum conversion efficiency is obtained if electrical circuit 26 incorporates an appropriate matching network.

Efficient electro-acoustic conversion is also possible when the thickness of the non-shorted layers composing the resonant cavity is an odd number of half-wavelengths. In this case, electro-acoustic interaction normally takes place both between the electric port and each of the acoustic ports, and between the acoustic ports themselves. However, if desired, it is possible to restrict energy flow to that between the electrical port and only one of the acoustic ports, if the other acoustic port is placed in contact with air to provide an effective acoustic short-circuit. Again, electro-acoustic conversion efficiency can be enhanced by incorporating an appropriate matching network in electrical circuit 26.

A special case exists when the thickness of the non-shorted layers is an even number of full wavelengths. In this case, no energy transfer is possible. This is because the reflection coefficient is unity at all ports, so that unit 10 now operates as a band-rejection filter in which all signals at all ports are rejected.

Figure 4:
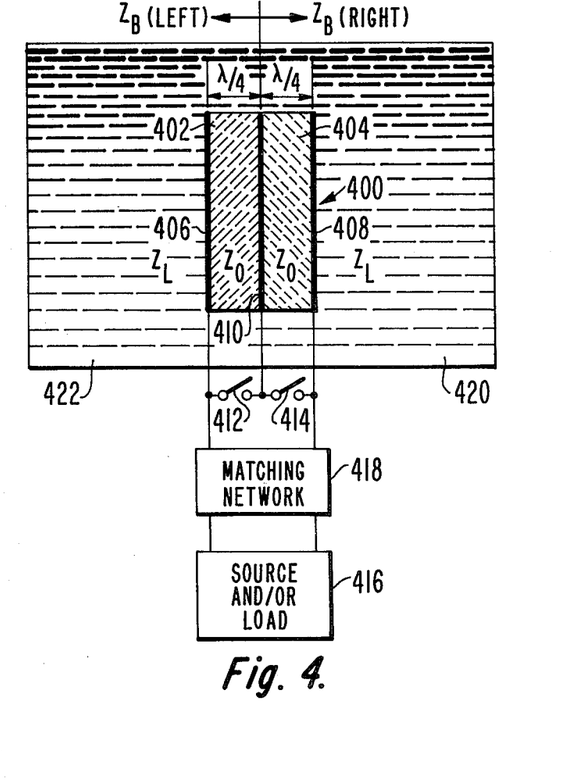
FIG. 4 is a block diagram of a first acoustic wave propagating system utilizing a specific embodiment of the acoustic wave energy control device of the present invention.

FIG. 4 shows the use of a two-layered piezoelectric unit as a switchable directional acoustic coupler for acoustic wave energy of a given frequency. Specifically, two-layers of piezoelectric unit 400 comprise contiguous left and right piezoelectric layers 402 and 404, each having a thickness of one-quarter wavelength for acoustic wave energy propagating therein. Unit 400 further comprises first electrode 406 at the outer face of left layer 402; second electrode 408 at the outer face of right layer 404, and additional electrode 410 at the interface between layers 402 and 404.

Figure 4A:
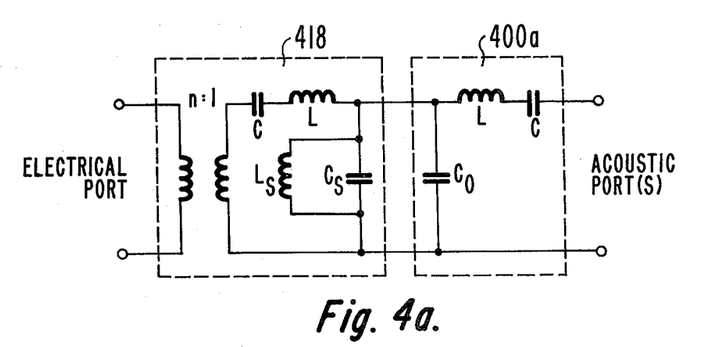
FIG. 4a shows an electrical equivalent circuit of the piezoelectric unit of FIG. 4 together with the electrical circuit of a matching network therefor.

Switch 412, connected between first electrode 406 and additional electrode 410, is selectively operable to short circuit left layer 402. Similarly, switch 414, connected between second electrode 408 and additional electrode 410, is selectively operable to short circuit right layer 404. First and second electrodes 406 and 408 are coupled to an electrical source and/or load 416 through electrical matching network 418. An example of matching network 418 is shown in FIG. 4a discussed below. As is known in the art, an impedance matching network is inserted between two coupled circuits exhibiting different impedances to ensure maximum power transfer therebetween. Thus, in the special case where the impedance of block 416 is substantially the same as that of unit 400, matching network 418 may be omitted.

As shown in FIG. 4, unit 400 is immersed in a water medium (which exhibits a relatively low impedance $Z_L$ discussed above). The intrinsic impedance of the piezoelectric material, such as PZT−4, of each of quarter-wavelength layer 402 and 404 is more than 20 times as high as the impedance $Z_L$ (as discussed). Therefore, in accordance with the equation (2), either of these layers, when short circuited, presents a sufficiently high impedance Z to act as a rigid backing to the non-short-circuited quarter-wavelength layer. Therefore, this other one of this quarter-wavelength layers is in a condition to operate as an efficient electro-acoustic transducer between the water medium at its outer face and the source and/or load 416 coupled to its electric port.

Thus, with switch 412 closed and switch 414 open and block 416 is a source, acoustic wave energy is launched only in region 420 of the water medium to the right to unit 400 and not in region 422 of the water medium to the left of device 400. Similarly, if block 416 is a load, device 400 absorbs acoustic wave energy present in region 420, but not in region 422. On the other hand, if switch 412 is opened and switch 414 is closed, the situation is reversed, so that acoustic wave energy is launched or absorbed, as the case may be, from region 422 of the water medium to the left of unit 400, but not from region 420 to the right of unit 400. In this manner, unit 400 operates as a directional coupler.

In addition to its operation as a directional coupler, unit 400 may operate as a gate. Specifically, if both switches 412 and 414 are closed at the same time, two-layer unit 400 (which has an overall thickness of one-half wavelength) operates as a substantially transparent transmission medium in accordance with equation (3) above. This permits acoustic wave energy present in right region 420 to be transmitted to left region 422, or vice versa. Finally, if both switches 412 and 414 are open at the same time, two-layered unit 400 (having an overall thickness of one-half wavelength) operates as an efficient electro-acoustic transducer for simultaneously launching acoustic wave energy into or absorbing acoustic wave energy from both right region 420 and left region 422.

Referring now to FIG. 4a, there is shown the electrical equivalent circuit of transducer 400 together with a specific example of the circuitry of matching network 418. As shown, the electrical equivalent circuit 400a is composed of an L-C series circuit resonant at the nominal operating frequency. However, the series resonant circuit is shunted by a capacitance $C_O$ (the capacitance between the electrodes). Matching network 418 includes a corresponding LC resonant circuit, which has a parallel $L_s - C_s$ circuit shunting the capacitance $C_O$ of equivalent circuit 400a. Inductance $L_S$ with the total capacitance $C_s + C_O$ forms a very high shunting impedance parallel resonant circuit at the operating frequency of the transducer. Matching network 418 further includes an impedance transformer having a turn ratio between primary and secondary equal to $n:1$, the value of the $n$ being selected to appropriately increase or decrease, as the case may be, the termination impedance of source 416 to a value equal to the electrical equivalent of impedance $Z_L$ terminating the acoustic port or ports of device 400. Blocks 418 and 400a together form a constant K filter.

Figure 5:
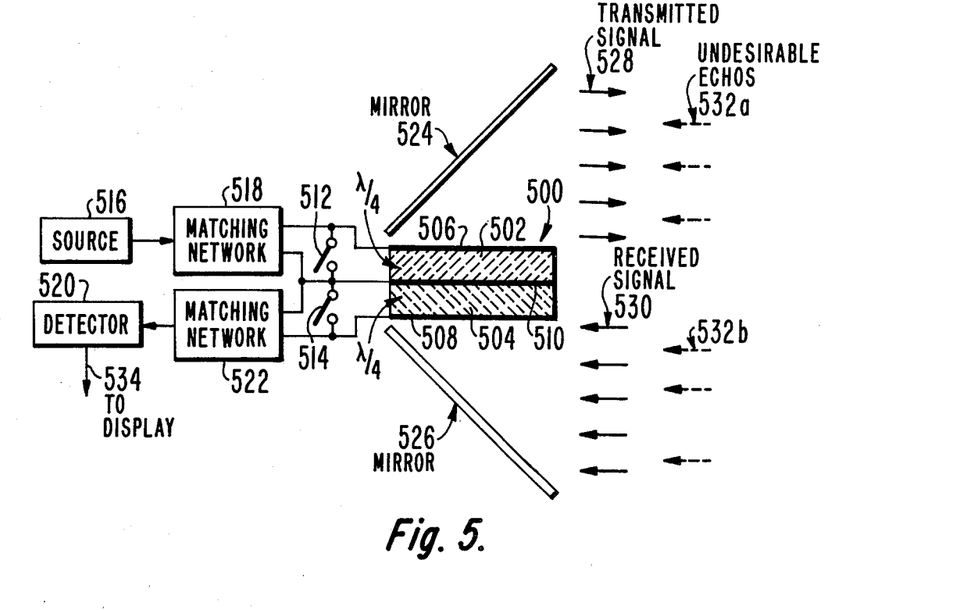
FIG. 5 illustrates a second acoustic wave propagating system incorporating a specific embodiment of the present invention.

Referring now to FIG. 5, there is shown an arrangement of the present invention, which also employs two contiguous quarter-wavelength piezoelectric layers, which is useful in separating the transmit and receive functions in an ultrasonic wave pulse-echo imaging system. As is known in the art, in such a system successive pulses of ultrasonic wave energy are launched in a liquid medium, such as water, by an electro-acoustic transducer at a predetermined repetition rate. The acoustic wave may be focused and/or scanned by suitable means (not shown in FIG. 5). The acoustic wave is used to probe a region of a given object and acoustic echos received from the region by the transducer are detected as the desired signal and applied to a suitable display device, such as a CRT. By way of example, various embodiments of the resolution pulse-echo ultrasonic imaging display system are disclosed in copending U.S. patent application Ser. No. 766,564, filed Feb. 7, 1977 by Mezrich et al., and assigned to the same assignee as the present invention.

In a pulse-echo imaging system, the desired received signal occurs at a time delay with respect to the transmitted pulse that is equal to the round-trip travel time of the ultasonic wave energy between the transducer and the region of the object being probed. An inherent problem of such a system is that the transducer also responds to undesirable echos received both before and after the occurence of the desired received signal. The conventional solution of this problem is to provide an electronic range gate between the transducer and the display. This range gate is open only during the time of occurrence of the desired received signal to prevent undesirable echoes detected by the transducer from reaching the display and thereby resulting in spurious display information. However, the energy within the transducer derived from the undesirable echoes received and detected thereby must still be dissipated. Such dissipation of energy cannot take place instantly, but takes time. This is particularly true because the transducer forms a resonant cavity which is resonant at the frequency of the acoustic wave energy of the undesirable echoes (as well as that of the echoes which form the desired received signal). Therefore, there is a tendency for the transducer to ring in response to the detection of undesirable echoes. This ringing of undesirable echo energy normally persists into the time window during which the electronic range gate is open, thereby reducing the sensitivity and signal-to-noise ratio with which the desired received signal can be displayed. The arrangement shown in FIG. 5 overcomes this problem.

Specifically, two-layered unit 500, comprising contiguous top and bottom piezoelectric quarter-wavelength layers 502 and 504, first and second electrodes 506 and 508 and additional electrode 510 is intrinsically identical in structure and function with unit 400 described above. Similarly, switches 512 and 514, for selectively short-circuiting top layer 502 and bottom layer 504, are identical in structure and fraction to switches 412 and 414. However, in FIG. 5, the electrical circuit comprises source 516, which is coupled solely between first electrode 506 and additional electrode 510 by matching the network 518, and detector 520, which is coupled solely between second electrode 508 and additional electrode 510 by matching network 522. In addition, first mirror 524 is oriented above top layer 502 and second mirror 526 is oriented below bottom layer 504. In the specific embodiment shown in FIG. 5, each of mirrors 524 and 526 is a single, fixed, plane mirror oriented at 45° with respect to the axis of the system. However, modifications of the mirror sub-system in which each of the mirrors consists of an array of mirror elements, or in which one or both of the mirrors are curved, or in which one or both of the mirrors are tilted during each pulse repetition period, (or including other similar modifications within the sill of the art) are contemplated by the present invention.

In any case, switches 512, and 514 are operated as range gates. Specifically, switch 514 is open and switch 512 is closed only during the time window during which the desired received signal reaches unit 500. At all other times, switch 512 is open and switch 514 is closed.

Thus, based on the discussion in the connection with FIG. 4, each time that source 516 applies a pulse to the electric port of unit 500, unshort-circuited top layer 502 operates as an efficient electro-acoustic transducer, while short-circuited bottom layer 504 operates as a rigid wall. The acoustic wave energy transmitted by top layer 502 is reflected from mirror 524 to provide a transmitted signal 528 which propagates toward a region of a reflecting object under scrutiny. During a first time interval extending from the transmission of an acoustic pulse from unit 500 to the arrival of desired received signal 530 thereat, top layer 502 operates as an efficient electro-acoustic transducer for converting the acoustic energy of undesirable echoes 532a, deflected from mirror 524 back to top layer 502, into an electrical signal at its port. This electrical signal is returned to source 516, which now operates as a resistive load for dissipating the energy derived from undesirable echoes 532a. At the same time, the acoustic energy of undesirable echoes 532b reflected from mirror 526 and arriving at bottom layer 504 is substantially totally reflected therefrom. Most of this acoustic wave energy reflected from bottom layer 504 during the first time interval ultimately arrives at top layer 502 before the end of the first time interval. Thus, during the entire first interval, top layer 502 continuously operates to such up the dissipate the acoustic energy originally present in both undesirable echoes in 532a and 532b.

However, during the entire first time interval short circuited bottom layer 504 is effectively clamped so that it (1) absorbs substantially no acoustic wave energy and (2) is not capable of ringing. At the end of the first time interval, the range gate is open so that now top layer 502 is short-circuited and bottom layer 504 is unshort-circuited for the length of a time window during which acoustic wave energy of received signal 530 reflected from mirror 526 arrives at bottom layer 504. During this time window, bottom layer 504 operates as an efficient electro-acoustic transducer to provide an electrical signal at its electrical port which is forwarded through matching network 522 to detector 520. The signal arriving at detector 520 comprises substantially no noise components derived from undesirable echoes 532 and 532b. Therefore, output 534 of detector 520, which is forwarded to the display, has a relatively high sensitivity and signal-to-noise ratio. During a second time interval, which follows the time window, unit 500 reverts to the conditions initially present during the first time interval.

Figure 6:
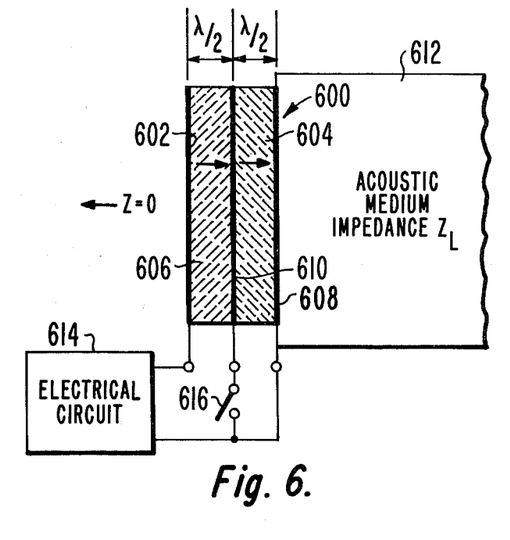
FIG. 6 illustrates the third acoustic wave propagating system incorporating a specific embodiment of the present invention.

FIG. 6 shows a unit 600, comprising two contiguous one-half wavelength layers 602 and 604, for use as a space-gated transducer. Specifically, first electrode 606 is at the outer face of left half-wavelength piezoelectric layer 602 second electrode 608 is at the outer face of right half-wave-length piezoelectric layer 604, and additional electrode 610 is at the interface between layers 602 and 604. A medium, such as air, having an acoustic impedance of substantially zero, is present at the outer face of left layer 602. An acoustic medium 612, such as water, having an acoustic impedance $Z_L$ is present at the outer face of right layer 604. Electrical circuit 614, which may include a source and/or detector, is coupled across first and second electrodes 606 and 608. Switch 616, connected between second electrode 608 and additional electrode 610, selectively short-circuits right layer 604.

When switch 616 is open, additional electrode 610 has no effect and the total thickness of control device 600 is one full wavelength. As discussed above, an unshortcircuited piezoelectric layer of an even number of full wavelengths operates as a band reject filter which isolates each of the two acoustic ports and the electric port of a piezoelectric unit from each other. Thus, in this case, the gated transducer formed by unit 600 is in its open condition, so that an electrical signal from circuit 614 having a frequency corresponding to one full wavelength of the total thickness of control device 600 does not launch an acoustic wave in medium 612. At the same time, an acoustic wave present in acoustic medium 612 does not five rise to a voltage across first and second electrodes 606 and 608.

The closure of switch 616 short circuits right layer 604, but leaves left layer 602 unshortcircuited. This results in the opening of the gates transducer formed by unit 600. Specifically, a signal source within circuit 614 may now apply a signal between first electrode 606 and additional electrode 610 solely to unshorted half-wavelength left layer 602, which operates as an efficient electro-acoustic transducer to generate an acoustic wave. Short-circuited half-wavelength right layer 604 operates as a transmission medium for the acoustic wave propagated to the right towards acoustic medium 612. No acoustic wave energy is propagated to the left because the left acoustic port of layer 602 is effectively short-circuited by the substantially zero acoustic impedance present thereat.

Figure 7:
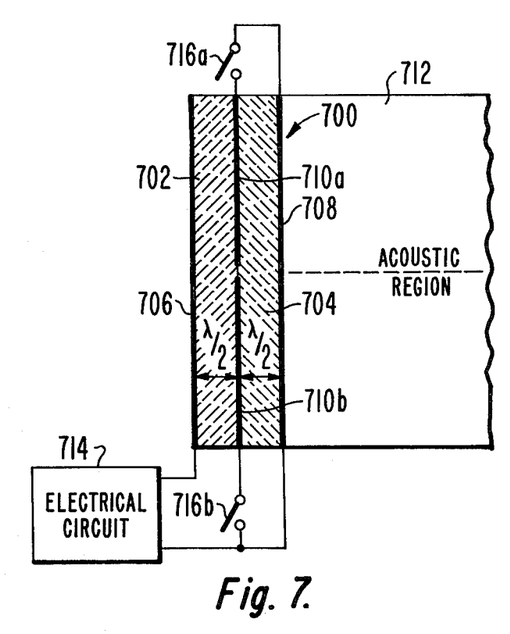
FIG. 7 illustrates a fourth acoustic wave propagating system incorporating a specific embodiment of the present invention.

Referring to FIG. 7, unit 700 is identical to control device 600 in all respects except that single additional electrode 610 at the interface of the two layers of FIG. 6 is replaced in FIG. 7 by separate spaced upper and lower additional electrodes 710a and 710b at the interface between the two layers in FIG. 7. In addition, separate switches 716a, connected between upper additional electrode 710a and second electrode 708, and switch 716b, connected between lower additional electrode 710b and second electrode 708, selectively short-circuit the upper and lower halves, respectively, of right layer 704.

By opening both switches 716a and 716b or closing both switches 716a and 716b unit 700 operates in a manner identical to that described in connection with FIG. 6 to launch or receive any acoustic wave in region 712. However, the arrangement of FIG. 7 has the further ability to selectively launch or receive an acoustic wave solely in the upper or solely in the lower half of region 712 by selectively closing either (but not both) switch 716a or switch 716b.

The aforesaid copending U.S. patent application Ser. No. 766,564, in FIGS. 6 and 6a thereof, shows a space-divided embodiment of a scanning ultrasonic source and detector for providing real-time scanning of a target area to be displayed by appropriate imaging electronics. An improved transducer for use in such a space-divided embodiment is shown herein in FIG. 8. Unit 800 forms this improved transducer.

Figure 8:
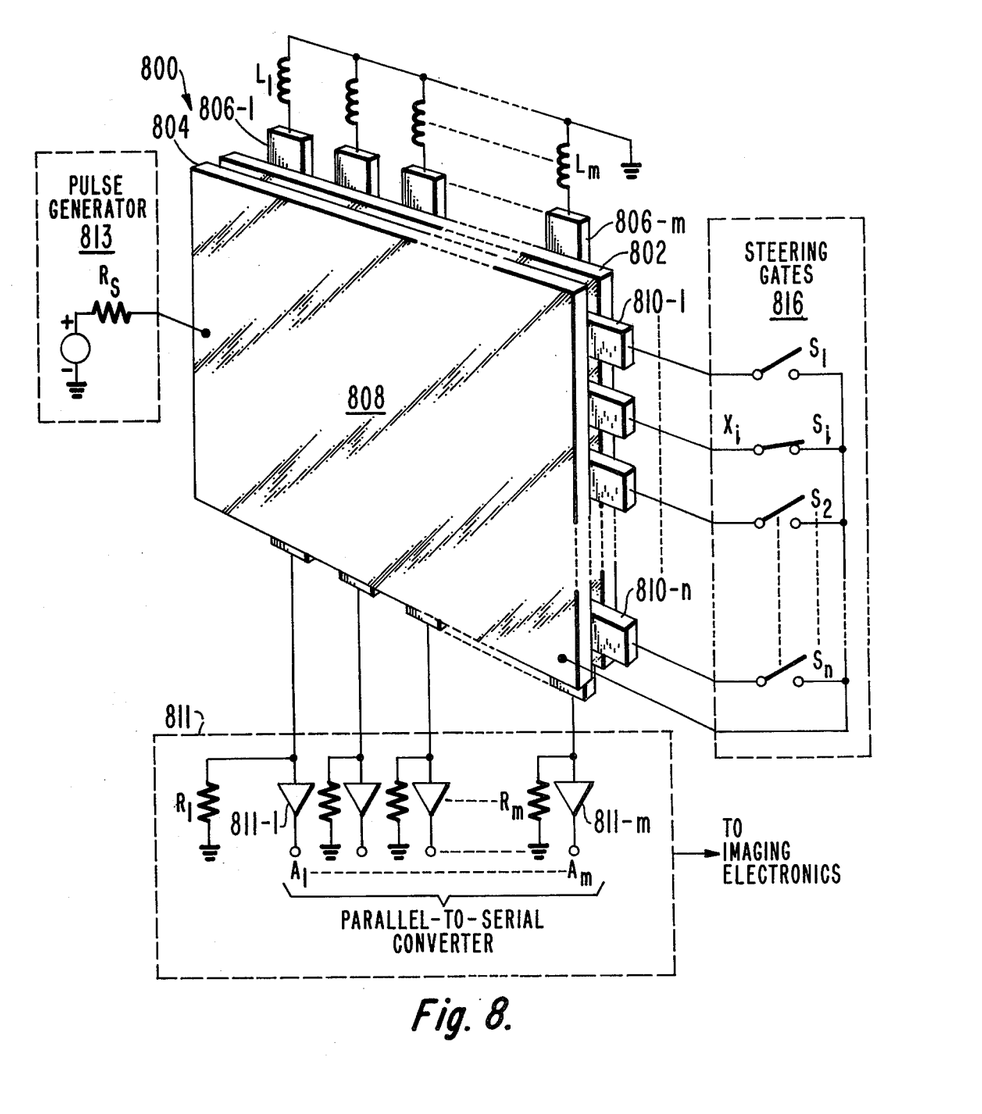
FIG. 8 illustrates a fifth acoustic wave propagating system incorporating a specific embodiment of the present invention.

Specifically, unit 800 comprises two contiguous one-half wavelength layers 802 and 804. A set of $m$ spaced vertical electrodes 806-$1$ ... 806-$m$ are at the outer face of rear layer 802, second electrode 808 is at the outer face of front layer 804, and a set of $n$ additional electrodes 810-$1$ ... 810-$n$ is at the interface between layers 802 and 804.

Parallel-to-serial converter 811 comprises a set of load resistances $R_1 \ldots R_m$ connected between corresponding ones of first electrodes 806-1 ... 806-m and a point of reference potential. Parallel-to-serial converter 811 further includes a set of amplifiers 811-1 ... 811-m which respectively amplify any signal developed across the corresponding one of load resistance $R_1 \ldots R_m$. The outputs $A_1 \ldots A_m$ from the set of amplifiers is applied in parallel to a set of storage means, (not shown). These storage means are then serially read out, as described in the aforesaid U.S. patent application Ser. No. 766,546. In addition, the set of first electrodes 806-1 ... 806-m are coupled to the point of reference potential through corresponding ones of a set of inductances $L_1 \ldots L_m$.

Pulse generator 813 is coupled between second electrode 808 and the point of reference potential. Further, a set of steering gates 816, composed of switches $S_1 \ldots S_n$, is connected between second electrode 808 and corresponding ones of additional electrodes 810-1 ... 810-n to short-circuit a corresponding horizontal linear segment of front layer 804.

Rear layer 802, per se, together with the sets of first electrodes 806-1 ... 806-m and the set of additional electrodes 810-1 ... 810-n correspond with the single-layered transducer shown in FIGS. 6 and 6a of the aforesaid U.S. patent application Ser. No. 766,564. As disclosed therein, the set of vertical electrodes and the set of horizontal electrodes define $m$ times $n$ cross points. The region of layer 802 defined by each individual cross point is capable of operating as a discrete electro-acoustic transducer element.

The operation of the embodiment of FIG. 8 employs the principles discussed above in connection with FIGS. 6 and 7 hereof. Specifically, only the particular horizontal row of transducer elements $X_i$ associated with the then closed one $S_i$ of switches $S_1 \ldots S_n$ are then effective as efficient electro-optic transducers, because for these particular horizontal rows of transducer elements front half-wavelength 804 is then in a short-circuited condition. However, all the remainder of the $m$ times $n$ transducer elements, associated with all the then open ones of switches $S_1 \ldots S_n$, are ineffective at this time. This is because unshortcircuited half-wavelength front layer 804 together with unshortcircuited half-wavelength rear layer 802 form a full-wavelength cavity for these remainder of the the transducer elements. The electric port and the two acoustic ports of each remainder transducer element associated with an open switch are, therefore, decoupled from each other for the reasons discussed above in connection with the full wavelength acoustic cavities.

Each of the set of inductances $L_1 \ldots L_m$ has substantially the same given value. This given value is selected to form a resonant circuit at the operating frequency with the shunt capacitance between second electrode 808 and the corresponding one of each one of the first electrodes 806-1 ... 806-m. This prevents the relatively low shunt capacitance reactance from bypassing the signal applied to or derived from each then-effective transducer element associated with the closed switch $S_i$.

The prior art transducer employed in FIGS. 6 and 6a of the aforesaid U.S. patent application Ser. No. 766,564 employs only a single piezoelectric layer corresponding to rear layer 802, and omits front layer 804, second electrode 808 and the set of inductances $L_1 \ldots L_n$. In other respects, the structure of this prior art transducer is essentially similar to that of FIG. 8. Functionally, this single-layered prior art transducer exhibits a significant effective shunting parasitic load impedance between the set of first electrodes thereof (corresponding to electrodes 806-1 ... 806-m) and the point of reference potential.

This shunting parasitic load impedance in the prior art tends to reduce the effective sensitivity and raises the effective signal-to-noise ratio of sensed signals forwarded by the set of first electrodes to the input of the prior art parallel-to-serial converter, which corresponds with converter 811). Further, the greater the total number of $m \cdot m$ cross-points, the greater is the effect of the shunting parasitic load impedance in this prior art transducer.

The effective shunting parasitic load impedance of the improved transducer embodiment shown in FIG. 8 is substantially eliminated. This results in a piezoelectric array having substantially no cross-coupling between individual transducer elements thereof. By way of example, in practice, this resulted in an improvement of as much as 34 dB in the sensitivity of a 100 times 100 cross-point piezoelectric array incorporating the present invention, compared to a similar single-layered prior-art piezoelectric array transducer.

What is claimed is:

1. A variable acoustic wave energy transfer characteristic control device including:
   a piezoelectric unit comprising a plurality of contiguous layers of piezoelectric material which define two outer faces and define an interface between each pair of adjacent ones of said contiguous layers, each of said layers having a respective specified thickness, first and second electrodes respectively at said outer faces, and at least one additional electrode at each interface;
   an electrical circuit connected across said first and second electrodes; and
   switch means for selectively connecting said at least one additional electrode to another one of said electrodes which selectively short circuits at least a portion of at least one of said layers of said piezoelectric element.

2. The control device defined in claim 1, wherein said piezoelectric unit comprises solely two contiguous layers of piezoelectric material.

3. The control device defined in claim 2,
   wherein said acoustic wave energy includes a given operating frequency, and
   wherein each of said two contiguous layers has a respective specified thickness equal to an odd number of quarter-wavelengths of acoustic wave energy of said given operating frequency therein.

4. The control device defined in claim 3,
   wherein said piezoelectric material exhibits a given acoustic impedance,
   wherein said outer face of said first layer and said other face of said second layer are coupled to an acoustic propagating medium exhibiting a relatively small acoustic impedance with respect to said given acoustic impedance so that a short circuited one of said two layers reflects substantially all acoustic wave energy of said operating frequency incident thereon, and
   wherein said switch means includes first and second switches, said first switch connecting a single additional electrode at the interface between said two layers to said first electrode to selectively short-circuit a first of said two layers, and said second switch connecting said single additional electrode to said second electrode to selectively short-circuit a second of said two layers.

5. The control device defined in claim 4,
wherein said electrical circuit includes a source coupled solely between said first electrode and said single additional electrode for applying a transmit pulse signal at said operating frequency to said first layer at a given time, and includes a detector coupled solely between said second electrode and said single additional electrode,
first mirror means situated to deflect an incident transmitted pulse signal of acoustic wave energy from the outer face of said first layer toward a given remote acoustic wave reflecting region, second mirror means situated to deflect received echo signals from said given region toward the outer face of said second layer, and
said switch means maintaining said first switch closed and said second switch open only during a time window in which said received echo signals arrive at said second layer, said switch means maintaining said second switch closed and said first switch open during a time interval extending from said given time to the beginning of said time window.

6. The control device defined in claim 5, wherein said switch means further maintains said second switch closed and said first switch open for a second time interval following the end of said time window.

7. The control device defined in claim 2
wherein said acoustic wave energy includes a given operating frequency, and
wherein each of said two contiguous layers has a respective specified thickness equal to an odd number of half-wavelengths of acoustic wave energy of said given operating frequency therein.

8. The control device defined in claim 7,
wherein said piezoelectric materials exhibits a first given acoustic impedance,
wherein said outer face of said first layer is coupled to a medium exhibiting substantially zero impedance and said outer face of said second layer is coupled to an acoustic propagating medium exhibiting a second given impedance,
wherein said electrical circiut responds to said given operating frequency, and
wherein said switch means includes a switch connected between an additional electrode at the interface between said first and second layers and said second electrode for selectively short-circuiting at least a portion of said second layer.

9. The control device defined in claim 8,
wherein said piezoelectric unit includes at least two spaced additional electrodes at the interface between said first and second layers, and
wherein said switch means includes at least first and second switches, said first switch being connected between a first of said additional electrodes and said second electrode for selectively short-circuiting a first portion of said second layer whose location is defined by the position of the first of said additional electrodes, and said second switch being connected between a second of said additional electrodes and said second electrode for selectively short-circuiting a second portion of said second layer whose location is defined by the position of the second of said additional electrodes.

10. The control device defined in claim 9,
wherein said first layer has a set of $m$ spaced linear first electrodes at said outer face thereof, $m$ being a first given integer, all of said first electrodes being oriented in a first direction which is substantially parallel to a given line, and
wherein said piezoelectric unit includes a set of $n$ spaced linear additional electrodes at the interface between said first and second layers, $n$ being a second given integer, all of said additional electrodes being oriented in a second direction which is substantially perpendicular to said given line, and
wherein said switch means includes $n$ switches each of which is connected between a corresponding one of said $n$ additional electrodes and said second electrode for selectively short-circuiting a portion of said second layer whose location is defined by the position of any one of said switches that is closed.

11. The control device defined in claim 10,
wherein said electrical circuit includes a source of pulse signal of said operating frequency connected between said second electrode and a point of reference potential, and a set of $m$ signal detectors respectively connected between corresponding ones of said $m$ first electrodes and said point of reference potential.

12. The control device defined in claim 11,
wherein said electrical circuit further includes a set of $m$ inductances respectively connected between corresponding ones of said $m$ first electrodes and said point of reference potential, said inductances being resonant with the shunt capacitance between said second electrode and said corresponding ones of said $m$ first electrodes at said operating frequency.

* * * * *

UNITED STATES PATENT OFFICE
CERTIFICATE OF CORRECTION

PATENT NO. : 4,096,756

DATED : June 27, 1978

INVENTOR(S) : Gerard Argant Alphonse

It is certified that error appears in the above-identified patent and that said Letters Patent are hereby corrected as shown below:

Column 1, line 45, "21" should be --$\underline{21}$--
Column 1, line 47, "21" should be --$\overline{21}$--
Column 1, line 51, "21" should be --$\overline{\underline{21}}$--
Column 3, line 14, "a" should be --$\overline{\underline{a}}$--
Column 4, line 22, "a" should be --$\overline{a}$--

Column 8, line 65, "sill" should be --skill--

Column 9, line 30, "such" should be --suck--

Column 10, line 20, "gates" should be --gated--
Column 11, line 11, "766,546" should be --766,564--

*Signed and Sealed this*

*Twenty-third* Day of *January 1979*

[SEAL]

Attest:

RUTH C. MASON
*Attesting Officer*

DONALD W. BANNER
*Commissioner of Patents and Trademarks*